United States Patent [19]

Ackermann et al.

[11] Patent Number: 4,787,980
[45] Date of Patent: Nov. 29, 1988

[54] ULTRA PURE WATER SYSTEM MONITORING

[75] Inventors: Arthur J. Ackermann, Kirkwood; Robert A. Craven, Olivette, both of Mo.

[73] Assignee: Monsanto Company, St. Louis, Mo.

[21] Appl. No.: 914,093

[22] Filed: Oct. 1, 1986

[51] Int. Cl.⁴ .............................................. B01D 13/00
[52] U.S. Cl. ..................................... 210/638; 210/652; 210/195.2
[58] Field of Search ................ 210/259, 85, 96.2, 638, 210/321.1, 805, 652, 195.2; 73/863.31; 422/102

[56] References Cited

U.S. PATENT DOCUMENTS

| | | |
|---|---|---|
| 4,473,475 | 9/1984 | Barnes, Jr. et al. .................. 210/638 |
| 4,517,160 | 5/1985 | Galle et al. ....................... 422/102 X |
| 4,517,849 | 5/1985 | Hakahuri et al. ................. 73/863.31 |

OTHER PUBLICATIONS

C. Nebel et al., Purification of Deionized Water by Oxidation with Ozone, Oct., 1984, Solid State Technology, pp. 185–193.

Robert Legan, Ultraviolet Light Takes on CPI Role, Jan. 25, 1982, Chemical Engineering, pp. 95–100.

*Primary Examiner*—Frank Spear
*Attorney, Agent, or Firm*—Paul L. Passley

[57] ABSTRACT

This invention is directed to a hydraulic multiplex unit for receiving continuously one or more samples of liquid from a liquid purification system of distribution system and redirecting such sample or samples randomly or in sequence to one or more analytical instruments. The sample collecting system and multiplex unit is periodically backflushed with ozone to maintain the collection and analysis system clean of impurities, particles and the like which adversely affect the composition of the fluid samples.

23 Claims, 5 Drawing Sheets

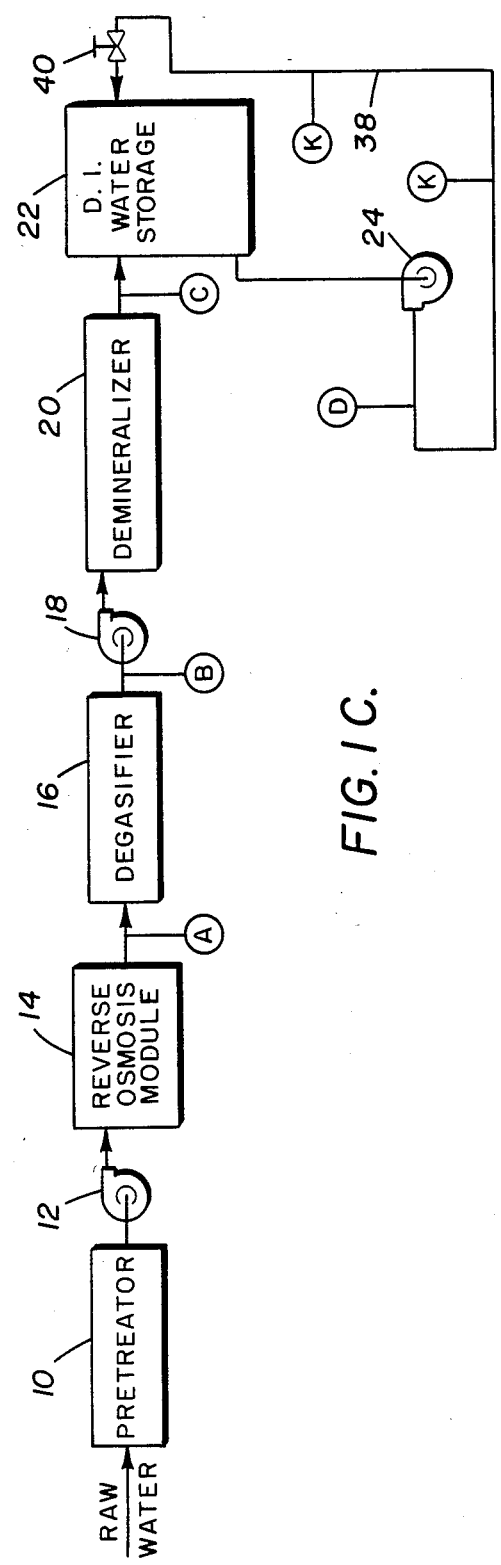
FIG. IC.

ULTRA PURE WATER SYSTEM MONITORING

BACKGROUND OF THE INVENTION

1. Field of the Invention

This invention relates to high purity liquid distribution systems. Particularly, this invention relates to means and methods for continuously monitoring the purity and consistency of the liquid product at selected points in the system of liquid purification or distribution system. Specifically, this invention relates to means for continuously receiving samples of ultra pure deionized water from one or more points in the purification or distribution systems and distributing these samples to a variety of analytical instruments. This invention is directed to the ability to deliver samples of liquid to analytical instruments which are truly representative of the liquid stream and which have not been adulterated by the sampling procedure or process.

Today, many industrial manufacturing processes require the use of ultra high pure waler either as a direct process fluid or as a the major component of a liquid product. This is particularly true of the pharmaceutical, electronic and electrical utilities industries. Purity of water used in the pharmaceutical industry is clearly apparent because of the human involvement in the final product. Greater and greater purity of water in the electronics industry is required due to the continuously greater miniaturization in the manufacture of electronic devices on semiconductor substrates such as single crystal silicon wafers. Impurities on the substrates in the region of the electronic device formation causes defects in the devices formed which may considerably lower the yield of good product from the manufacturing process. These impurities can also affect the long term reliability of the product manufactured. It is readily apparent that as greater and greater miniaturization of the device design occurs, there is a much greater need go insure removal of impurities, particulary impurities of smaller and smaller size, such as bacteria, bacterial fragments, inert debris and other micro-organisms. The utility industries have a continuously increasing need for high purity water products because of safety and economic issues associated with degradation of high pressure steam containment vessels and heat exchangers, and a variety of scaling and metallurgical problems associated with silicates and other metal corrosion problems.

2. Description of the Prior Art

The necessity for very clean water in the pharmaceutical, electronic and utility industries has been realized for a number of years and much effort has been expended to develope technology for the removal of both chemical and particulate impurities within liquid streams. Purification of water typically requires a variety of process steps with a particular type of impurity being eliminated at each step. FIG. 1 shows a typical water purification facility for electronic, pharmaceutical or utility industries. The execution of all of the process steps at their highest efficiency is required to reach the highest level of water purity at the lowest possible cost.

An additional relevant technology which as fairly recently been explored in water purification and use distribution systems is the use of ozone as an oxidant. A paper on this subject entitled "Purification of Deionized water by Oxidation with Ozone" by Carl Nebel and William W. Nezgod was published in the October 1984 issue of Solid State Technology starting on page 185. This article gives a very complete explanation of the unique properties of ozone for water treatment. In another article entitled "Ultraviolet Light Takes on CPI Role" by Robert E. Legan and published in Chemical Engineering, Jan. 25, 1982, the combination of ultraviolet light with ozone to sterilize water is reported. Without being redundant in the teachings of these articles, the reader is invited to review them for additional information and background.

Due to the formerly less stringent requirements for ultra pure water used in industrial processes, water systems in place are not generally designed or operated efficiently enough to heap the complete advantage of existing water purification technology. Significant improvements in the quality of water in systems in place and significant economics of the operations thereof are accordingly highly desired today. Improvements in sensitive and rapid analysis systems such as this invention which can access multiple process steps and distribution networks for ultra pure water and ultra pure water products can significantly improve both water quality and the economics of water purification and use distribution systems.

SUMMARY OF THE INVENTION

This invention is directed to a hydraulic system for collection and processing one or more samples of water liquids or of high purity liquid solutions, such as water based solution, from an industrial process using such liquid systems and from the liquid distribution system. The hydraulic system is capable of continuously collecting samples from a plurality of use points in a high purity liquid system and directing such collected samples continuously or intermittently to a plurality of analysis instruments to determine the purity of the liquid at the particular unit process or use point. Liquid is continuously flowing in the sample lines, either in a positive direction towards the analytical instruments or intermittently in a negative direction while the sample line is backflushed with ozone. The continuous motion and intermittent sanitization and oxidation are critical to the assurance that the liquid sample will accurately represent the purity of the liquid at the point being monitored and will not be significantly degraded by the effects of stagnation.

Typical objects of this invention are to provide:

1. An improved means and method for collecting and analysis of liquid samples from selected points of use within an industrial pure liquid systems.

2. The means for continuous sample collection from a liquid stream.

3. The means for total system analysis of a liquid purification system in an industrial environment.

4. The means for generation of analytical information necessary for the efficient and effective operation of a liquid purification and/or distribution system.

5. The means for process control of the purification of an extremely pure liquid.

6. The means for discovery of the impact of the pure liquid distribution system on other parts of an industrial production process.

Other objects, aspects and advantages of this invention will become apparent to those skilled in the art upon further study of this application and the appended claims.

In accordance with a specific embodiment of this invention, one or more sample streams of high purity liquid flows continuously through fluorinated tubing or piping from the process liquid system piping to a liquid sample multiplexer unit. Upon entering the multiplexer unit each liquid sample is directed to its own main tubing or piping header. The sample flows through the header to a drain or is recycled to the high purity liquid system unless valves positioned in each header are activated to direct the liquid sample to a particular monitoring and/or analyzing means. As noted previously, the continuous flow of liquid in the sample collection lines prevents organics, particulates or biological contaminants from adhering or accumulating on the internal surfaces of the sample piping which would then subsequently sluff or flake off into the liquid sample being monitored and/or analyzed. This debris would drive an unduly high contamination analysis for a particular sample in the industrial liquid system.

In order to insure that the sample collections entering the multiplexer unit are always representative of the monitoring points, the sample collection lines from the monitoring point to the multiplexer unit are in further accordance with this invention intermittently or periodically backflushed with ozone to kill any biological organisms, oxidize organic compounds and loosen particles attached to the internal walls of the sample piping.

As previously indicated in accordance with this invention one or more, actually any number permitted by the physical boundary available, sample collection lines or pipes run from each particular point in a pure liquid system for which one desires to have the quality of water monitored or periodically analyzed to a particular liquid header in the multiplex unit of this invention. The liquid sample flows from its header through a line or pipe having a plurality of valves position therein so that the liquid sample may be directed through a sample line or pipe to one or more particular analytical instruments or be allowed to pass on through and to a drain or recycled to the main pure liquid system. A further feature of this invention in addition to the multiple sampling and analyzing is that the resistivity or conductivity of each liquid sample entering the multiplex unit may be continuously measured and recorded. The liquid samples may be directed to any particular analyzer or analysis desired. Typical analysis for ultra pure water quality are total oxidizable carbon content (TOC), size and number distribution of particles down to 0.2 microns, silica levels or sanitation levels.

In accordance with this invention, the switching of samples streams within the multiplex unit to one or more analyzers can be operated manually or if desired can be operated on a continuous desired cycle by use of a suitable programmed computer control system. The results of the analysis of the liquid samples find use in trouble shooting problems areas of contamination in liquid streams and the results of the analysis can be used in controlling the type and amount of treatment needed to obtain the purity desired or required.

This invention finds particular utility in the electronics industry both in the manufacture of semiconductor substrate materials, such as silicon, on which electronic devices are formed as well as in the electronic device houses where the the electronic devices are formed on a silicon wafer. Both the silicon wafer and device processes are multistep and utilize ultra pure water at various steps in such processes. It is to be furher understood that although this invention has been discussed in relation to the pharmaceutical, electronic and electrical utility industries that it would be evenually applicable for use in any other industries where a continuous supply of ultra pure liquid is required for the processes involved. This would include liquids made from pure water such as parenterial solutions and also food processing liquids.

DESCRIPTION OF THE DRAWINGS

FIGS. 1A, 1B and 1C are block diagrams of typical industrial water purification systems and distribution systems with typical sampling points in the purification process and in the distribution system indicated.

Referring to FIG. 1A, raw water is pretreated using multi-media filters and some chemical injection in pretreatment state 10 and is then pumped via pump 12 to a reverse osmosis module 14 from where it is deasified by degasifier 16 and pumped by repressurization pump 18 to a demineralization stage 20 which comprises a cation, anion and mixed bed resins, or mixed bed resins alone. The demineralized water is stored in dionized water storage tank 22. The deionized water is repressurized by pump 24 and fed to polishing deionized exchange means 26 which comprise mixed beds of ion exchange resins such as a combination of cation and anion resins. The deionized water from means 26 is filtered by post filter 28 and then processed through ultraviolet lamps 30 for bacteria control and then through a final submicron filtration 32. The deionized water then is fed through distribution system loop 38 to selected points of use or recycled through back pressure regulator 40 to the dionized water storage tank 22. The system in FIG. 1A is typical for use in the electronics industry. Typical sampling joints in the water purification system are indicated at A, B, C, D, E and F and sampling points in the use distribution system loop 38 as G which may be one or a plurality of different points. Sampling joint Z provides for an analysis of the deionized water returning to storage tank 22.

Referring to FIG. 1B, raw water is processed as described above in FIG. 1A through pump 24. In the application of FIG. 1B, a system typically used in the pharmaceutical industry, the deionized water is pumped via pump 24 to submicron filter 42 and into still 44 which is pyrogen free. The hot distilled dionized water is fed through hot distribution system loop 36 to selected points of use or recycled through return line 38 and back pressure regulator 40 to the dionized water storage tank 22. Typical sampling points in the water purification system in addition to those indicated in FIG. 1A are indicated at H and I and sampling points in the use distribution not loop 36 as J which may be one or a plurality of different points. The deionized water from hot loop 36 is directed through a heat exchanger, not shown, to the desired point of use K.

Referring to FIG. 1C, raw water is processed as described above in FIG. 1A through pump 24. In the application of FIG. 1C, a system typically used in utility industries, the deionized water is pumped via pump 24 through distribution system loop 38 to selected points of use or recycled through back pressure regulator 40 to the dionized water storage tank 22. Typical sampling points in the water purification system are as described in FIG. 1A to point D and sampling points in the distribution system loop 38 as K which may be one or a plurality of different points.

Referring to FIG. 2, a condensed version of the water purification scheme shown in FIG. 1A is shown with the desired sampling points flowing directly to the sample collection and distribution multiplexer of this invention. The multiplexer 46 shown is capable of handling six sample streams directing them as desired to selected analytical instruments. Sample streams from points A, C, D, E, F and Z continuously flow to multiplexer 46. Multiplexer 46 selectively directs the samples to the selected analytical instruments for analysis, for example, resistivity 48, silica 50, total oxidized carbon (TOC) 52 and particles 54. The multiplexer 46 is controlled by a suitable controller 56 such as a Hewlett/Packard 900 series 310 controller.

Referring to FIG. 3, a schematic diagram of the multiplexer 46 sampling and valve arrangement for a single liquid sample steam from the water purification system and/or distributor system and direction of the sample to the appropriate analyzer. For a single sample, such as sample A from FIG. 1A. The sample flows through valve VA1 which controls the flows to the multiplexer 46 or to a drain. The sample flows into a resistivity cell RC for resistivity analysis and then on through valves VA3, VA4, VA5 and VA6 to rotometer R into collection vessel 58 from which it is pumped by pump 60 for recycle through distributor system 38 to the DI Storage Tank 22. Valves VA3, VA4, and VA5 are controlled by Controller 56 shown in FIG. 2 to direct the sample to the desired analyzer silica 50, particle 52 and TOC 54 for analysis or valves VA1, VA3, VA4, VA5 and VA6 for backflushing with ozone from ozone generator 62. Although, FIG. 3 shows a single sample valve system it is to be understood that the multiplexer will contain that number of sample inlet lines and valve systems as desired for monitoring the quality of fluid being purified and/or used. The valve system within the multiplexer for a plurality of samples to be continuously or periodically analyzed will contain the necessary value arrangements for directing each sample independently to each analytical instrument. The controller 56 show in FIG. 2 will be programmed to sequence the flows of samples to the analyzers as desired as well as the periodic backflushing of the sample lines with ozone as necessary.

Figure 1A:
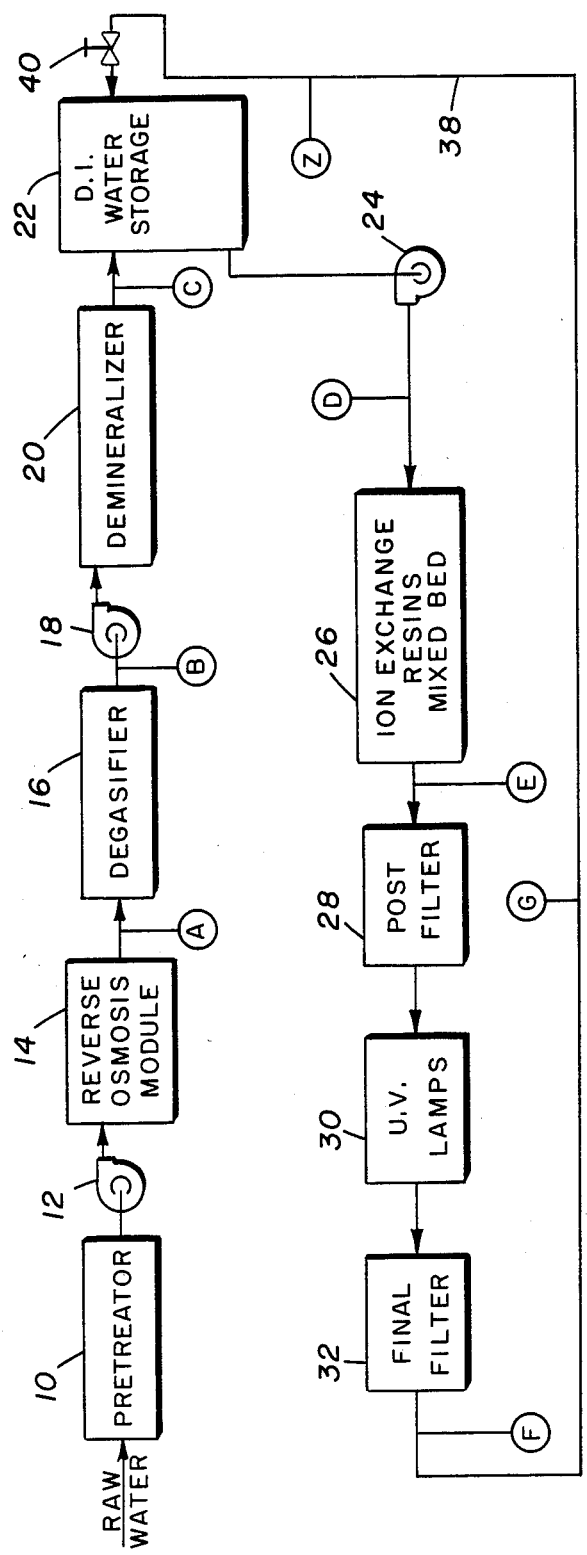
Figure 1B:
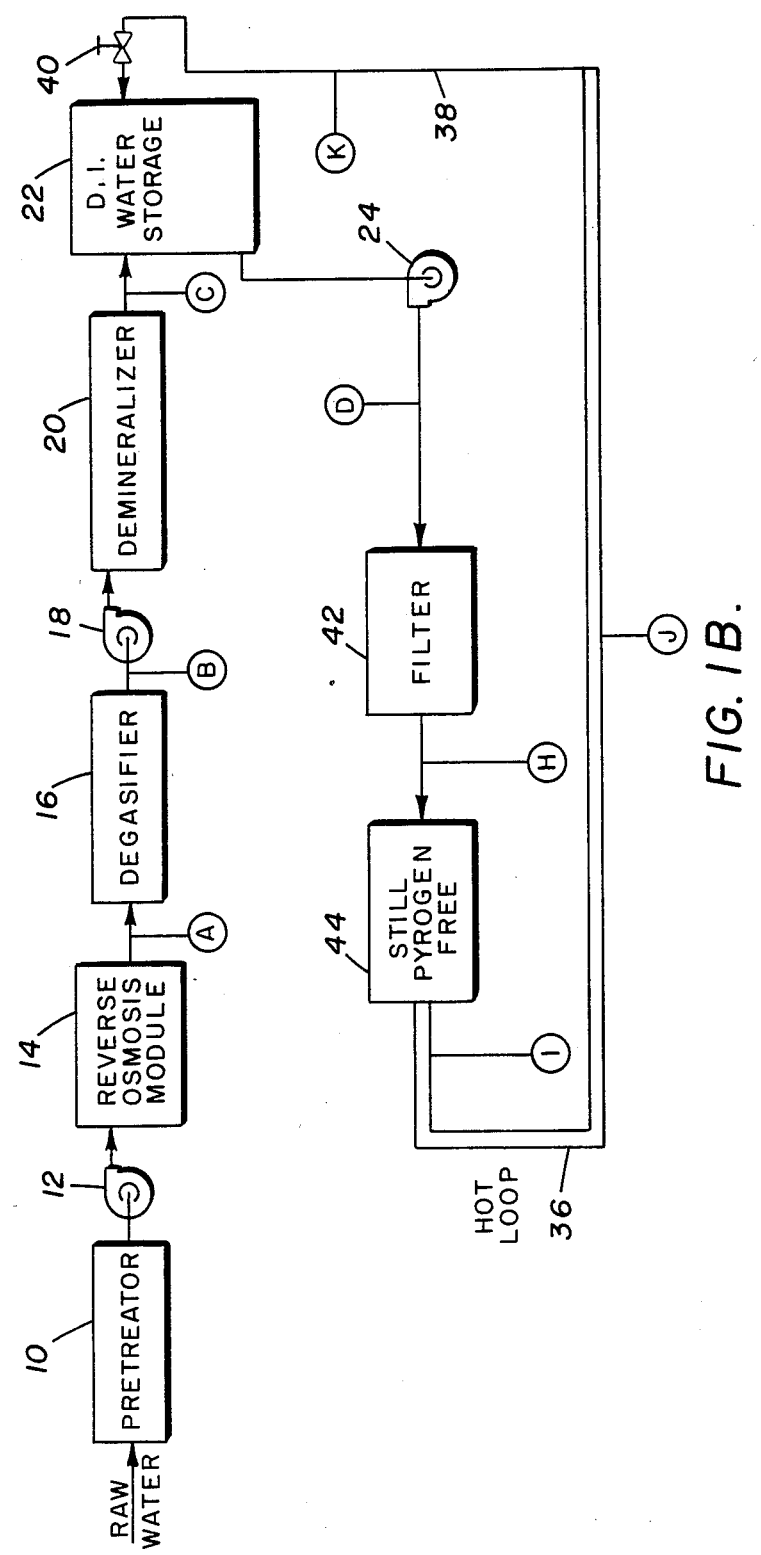
Figure 2:
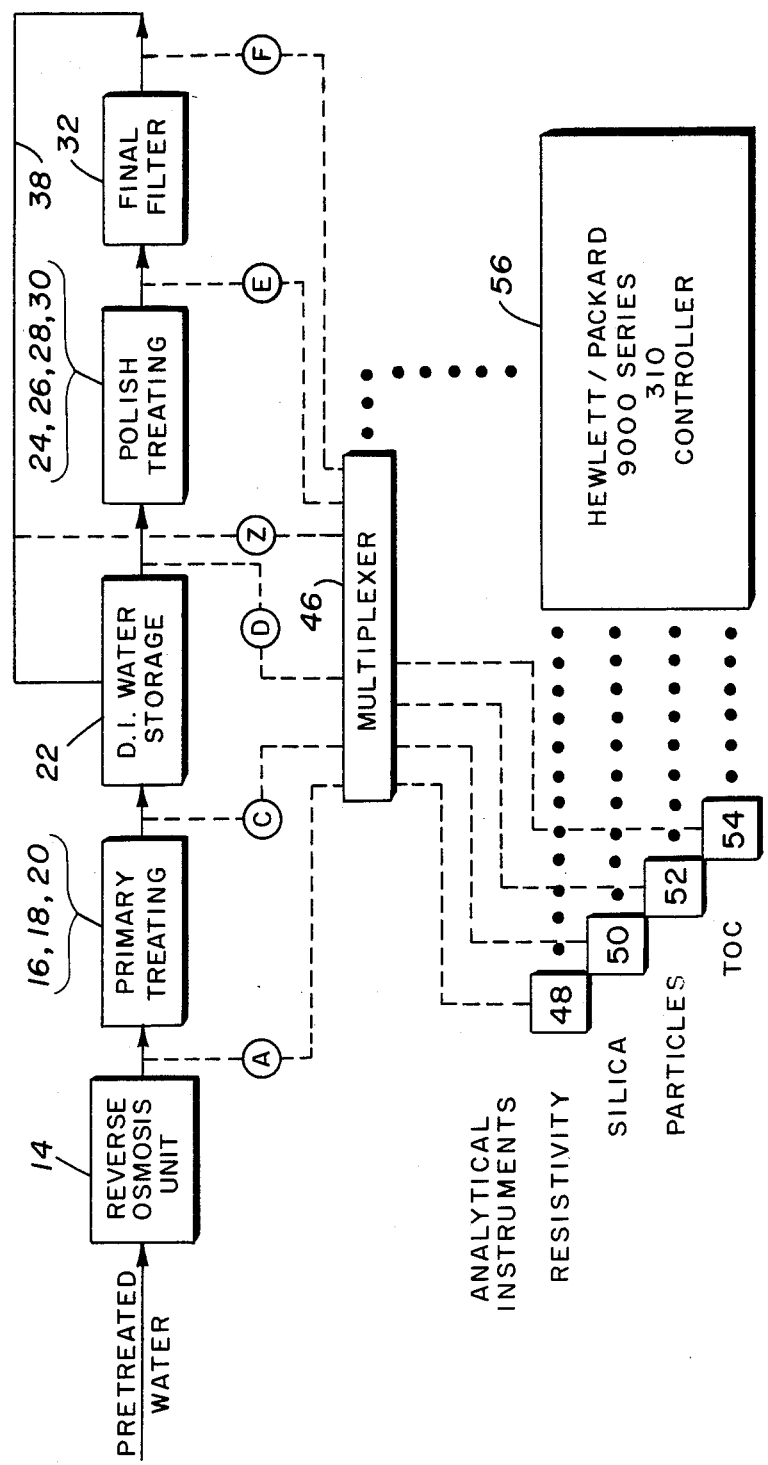
FIG. 2 is a block diagram of the liquid sample collecting and distribution to the multiplexer of this invention for redistribution to the selected analytical instruments.
Figure 3:
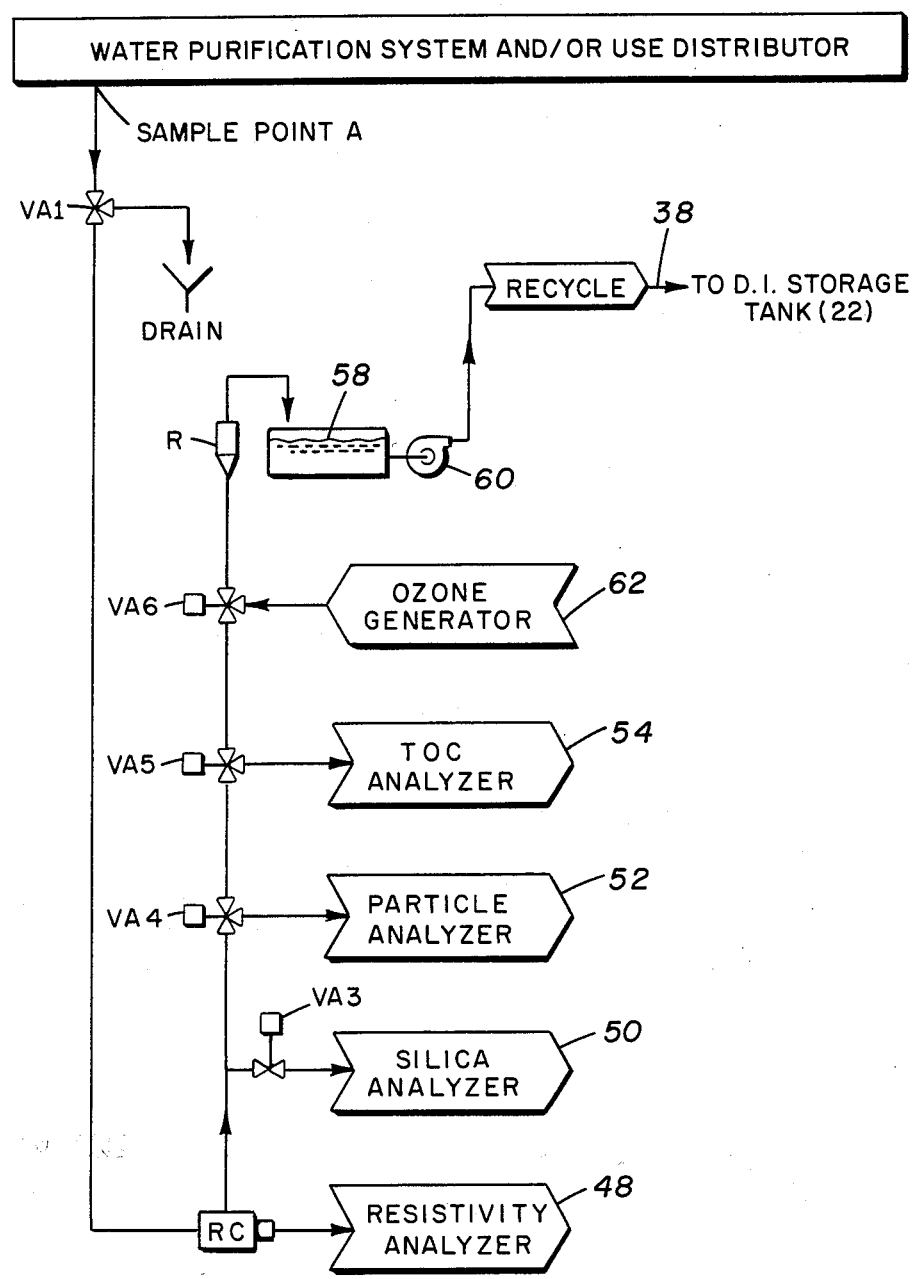
FIG. 3 is a schematic diagram of the multiplexer of this invention showing the collection and distribution of one liquid sample to the analytical instruments. The system shown would be duplicated for each additional liquid sample to be analyzed.

As previously indicated the multiplexer of this invention is a hydraulic sampling system for collecting samples of fluids from various locations with in fluid purification system and/or distribution system for the fluid and then directing the fluid streams to the desired analytical instruments for the desired analysis. The multiplexer is also provided with means for backflushing the sample lines with ozone to maintain them clean and noncontaminating as debris and particles fend to build up in the sample lines over time.

In operation one or more sample streams from a fluid purification system or distribution system loop flow through fluorinated tubing or piping from the purification system and/or distribution system loop to the multiplexer of this invention. Each sample stream flows continuously through a main header into and through the multiplexer. Valves are located on the main header for redirecting the sample flow to monitoring or processing equipment for analysis or particular use. When the sample stream is not to be directed to an analytical instrument or point of use, it flows through the main header to a drain or recycle collection vessel 58. However, when the redirecting valves are operated such as by controller 56 or manually if desired, the fluid flows continuously to the analytical instrument or point of use. The continuously flowing fluid within the sample lines considerably reduces organics, particles or biological contaminants from adhering or accumulating on the internal sample lines or piping. Controlling contamination in the sampling lines or piping because intermittent sluffing of contaminants will change the characteristic and quality of the water arriving at the multiplexer, analytical instruments and/or points of use.

As previously indicated over time, depending on the quality of the sample streams, even continuously flowing sample lines will gradually become contaminated. To clean the sample lines, in accordance with this invention, ozone gas or ozoninated water is back flushed manually or automatically through the sample lines or piping from the multiplexer to the fluid purification system or distributor system. Ozone being a strong oxiizing chemical will kill biological organisms, oxidize organic compounds and loosen particles attached to the internal walls of the sample lines or piping. After backflushing with ozone the sample streams are returned to continuously flowing from the purification system or distributor system to the multiplexer of this invention.

From the above description and the claims which follow this disclosure, it will probably be apparent to those skilled in the art that several if not many variations may be made and used in any actual equipment, analysis and use of the invention described herein which will be within this scope of this disclosure and will not depart from the spirit thereof.

What is claimed is:

1. A method of continuously sampling one or more points in a fluid purification system and/or in a distribution system loop for using the purified fluid and analyzing each sample for one or more characterizations comprising continuously feeding each sample stream to a multiplex unit and manipulating said multiplex unit to direct each continuous sample stream to the desired analytical instrument for analysis, or to a drain or recycled to the fluid purification system.

2. The method of claim 1 wherein said sample streams are continuously directed to a plurality of analytical instruments for analysis.

3. The method of claim 1 wherein said sample streams are continuously directed in sequence to a plurality of analytical instruments for analysis.

4. The method of claim 1 wherein the piping or lines containing said sample steams to said multiplexer are periodically backflushed with ozone gas or ozoninated fluid.

5. The method of claim 1 wherein said fluid is water which is purified and deionized.

6. The method of claim 1 wherein said method is used in the water purification system and use distribution system for processes in the electronics industry.

7. The method of claim 6 wherein said process is the production of electronic grade semiconductor substrates.

8. The method of claim 6 wherein said semiconductor substrates are silicon wafers.

9. The method of claim 1 wherein said method is used in the water purification system and distribution system loop for processes in the pharmaceutical industry.

10. The method of claim 1 wherein said method is used in the water purification system and distribution system loop for processes in the electrical utilities industry.

11. In the fluid purification system and distribution system loop of the purified fluid, the improvement comprising means for continuously obtaining fluid samples at one or more selected points in said purification and distribution systems and feeding said samples continuously to a multiplexer unit containing a valve system which is capable of being manipulated to direct the fluid samples to one or more analytical instruments for measuring a characteristic of said fluid samples or to a drain or recycled to the fluid purification system.

12. The improvement of claim 11 wherein said samples can be directed in parallel or in sequence or in random fashion to said analytical instruments.

13. The improvement of claim 11 wherein said samples are transported in fluorinated tubing or piping from said sample points in the purification and use distribution systems to the multiplexer means and onto the analytical instruments.

14. The improvement of claim 11 wherein means are provided for directing said sample streams to a drain or to recycle to the purification system when analysis thereof is not being obtained.

15. The improvement of claim 11 wherein said multiplexer valves are controlled by electronic means.

16. The improvement of claim 15 wherein said electronic means is a programmed electronic controller.

17. The improvement of claim 11 wherein said multiplexer valves are controlled manually.

18. The improvement of claim 11 wherein said fluid is water.

19. The improvement of claim 18 wherein said purification and distribution systems are used in the pharmaceutical industry.

20. The improvement of claim 18 wherein said purification and distribution systems are used in the electrical utilities industry.

21. The improvement of claim 11 wherein said purification and distribution systems are used in the manufacture of semiconductor wafers.

22. The improvement of claim 21 wherein said semiconductor substrates are silicon wafers.

23. The improvement of claim 11 wherein said multiplexer contains means for introducing ozone gas or ozonated fluid into the sample lines or piping for backflushing to remove impurities and contamination.

* * * * *

UNITED STATES PATENT AND TRADEMARK OFFICE
CERTIFICATE OF CORRECTION

PATENT NO. : 4,787,980

DATED : Nov. 29, 1988

INVENTOR(S) : Arthur J. Ackermann, Robert A. Craven

It is certified that error appears in the above-identified patent and that said Letters Patent is hereby corrected as shown below:

Column 2, line 15, "heap" should be --reap--.

Column 4, line 25, "deasified" should be --degasified--.

Column 6, line 23, "oxiizing" should be --oxidizing--.

Signed and Sealed this

Ninth Day of May, 1989

Attest:

DONALD J. QUIGG

Attesting Officer

Commissioner of Patents and Trademarks